US008439867B2

(12) United States Patent
Staskin

(10) Patent No.: US 8,439,867 B2
(45) Date of Patent: May 14, 2013

(54) INJECTION GUIDANCE SYSTEM AND METHOD

(76) Inventor: David R. Staskin, Boston, MA (US)

(*) Notice: Subject to any disclaimer, the term of this patent is extended or adjusted under 35 U.S.C. 154(b) by 809 days.

(21) Appl. No.: 11/921,724

(22) PCT Filed: Jun. 6, 2006

(86) PCT No.: PCT/US2006/021921
§ 371 (c)(1),
(2), (4) Date: Jul. 6, 2009

(87) PCT Pub. No.: WO2006/133193
PCT Pub. Date: Dec. 14, 2006

(65) Prior Publication Data
US 2009/0306590 A1   Dec. 10, 2009

Related U.S. Application Data

(60) Provisional application No. 60/688,213, filed on Jun. 7, 2005.

(51) Int. Cl.
*A61M 31/00*  (2006.01)
(52) U.S. Cl.
USPC ............ 604/103.01; 600/3; 600/37; 604/103; 604/103.02; 604/103.03; 604/103.04; 604/15; 604/41; 604/508; 604/21; 604/264; 604/507; 604/113; 604/890.1; 607/101; 607/99
(58) Field of Classification Search ............... 600/3, 37; 604/103, 103.01, 103.02, 103.03, 103.04, 604/15, 41, 101, 21, 264, 507, 508, 113, 604/890.1; 607/101, 99
See application file for complete search history.

(56) References Cited

U.S. PATENT DOCUMENTS

| 3,598,119 | A |   | 8/1971  | White |
| 4,430,076 | A | * | 2/1984  | Harris .................... 604/103.03 |
| 4,578,061 | A |   | 3/1986  | Lemelson |
| 4,976,711 | A | * | 12/1990 | Parins et al. .................... 606/48 |
| 4,998,930 | A |   | 3/1991  | Lundahl |
| 5,019,075 | A | * | 5/1991  | Spears et al. ...................... 606/7 |
| 5,088,979 | A | * | 2/1992  | Filipi et al. ...................... 604/26 |
| 5,152,754 | A | * | 10/1992 | Plyley et al. ............. 604/164.12 |
| 5,236,413 | A | * | 8/1993  | Feiring ........................... 604/21 |

(Continued)

FOREIGN PATENT DOCUMENTS

| DE | 4235506   | 4/1994  |
| GB | 2284158   | 5/1995  |
| WO | WO96/35464 | 11/1996 |

OTHER PUBLICATIONS

"The Anatomical Basis of Medicine and Surgery" *Gray's Anatomy* Edition 38 (1995).

*Primary Examiner* — Victoria P Shumate
*Assistant Examiner* — Scott Medway
(74) *Attorney, Agent, or Firm* — Moss & Barnett

(57) ABSTRACT

A system and method of treating urinary incontinence including a catheter and injection guide operatively disposed together. At least one needle is operatively disposed within at least one lumen and at least one channel extending through the catheter and injection guide respectively. The injection guide is transformable from a pre-injection configuration for placement in the bladder to an injection configuration for injection of a pharmaceutical such as botulinum toxin into the bladder tissue. Upon introduction of the pharmaceutical to the bladder tissue, symptoms of incontinence are alleviated.

20 Claims, 12 Drawing Sheets

U.S. PATENT DOCUMENTS

| | | | | |
|---|---|---|---|---|
| 5,236,424 | A | 8/1993 | Imran | |
| 5,255,678 | A * | 10/1993 | Deslauriers et al. | 600/375 |
| 5,258,390 | A | 11/1993 | Ohnmacht | |
| 5,282,785 | A * | 2/1994 | Shapland et al. | 604/21 |
| 5,301,688 | A | 4/1994 | Stephen et al. | |
| 5,328,467 | A * | 7/1994 | Edwards et al. | 604/95.01 |
| 5,419,777 | A | 5/1995 | Hofling | |
| 5,458,597 | A * | 10/1995 | Edwards et al. | 606/41 |
| 5,486,160 | A | 1/1996 | Rossi et al. | |
| 5,749,845 | A | 5/1998 | Hildebrand et al. | |
| 5,830,213 | A * | 11/1998 | Panescu et al. | 606/41 |
| 5,871,483 | A * | 2/1999 | Jackson et al. | 606/41 |
| 5,938,659 | A * | 8/1999 | Tu et al. | 606/41 |
| 6,002,968 | A * | 12/1999 | Edwards | 607/101 |
| 6,056,744 | A | 5/2000 | Edwards | |
| 6,197,013 | B1 * | 3/2001 | Reed et al. | 604/509 |
| 6,210,392 | B1 * | 4/2001 | Vigil et al. | 604/507 |
| 6,254,598 | B1 * | 7/2001 | Edwards et al. | 606/41 |
| 6,263,236 | B1 * | 7/2001 | Kasinkas et al. | 604/21 |
| 6,283,947 | B1 * | 9/2001 | Mirzaee | 604/264 |
| 6,306,163 | B1 * | 10/2001 | Fitz | 623/1.12 |
| 6,405,732 | B1 * | 6/2002 | Edwards et al. | 128/898 |
| 6,470,219 | B1 * | 10/2002 | Edwards et al. | 607/101 |
| 6,589,238 | B2 * | 7/2003 | Edwards et al. | 606/41 |
| 6,599,267 | B1 | 7/2003 | Ray et al. | |
| 6,623,473 | B1 | 9/2003 | Ponzi | |
| 6,625,486 | B2 * | 9/2003 | Lundkvist et al. | 604/21 |
| 6,685,648 | B2 * | 2/2004 | Flaherty et al. | 600/464 |
| 6,689,103 | B1 | 2/2004 | Palasis | |
| 6,872,206 | B2 * | 3/2005 | Edwards et al. | 606/41 |
| 6,918,869 | B2 * | 7/2005 | Shaw et al. | 600/3 |
| 7,273,469 | B1 * | 9/2007 | Chan et al. | 604/96.01 |
| 7,458,378 | B2 * | 12/2008 | Utley et al. | 128/898 |
| 7,470,252 | B2 * | 12/2008 | Mickley et al. | 604/103.02 |
| 7,473,252 | B2 * | 1/2009 | Barry | 606/41 |
| 7,708,752 | B2 * | 5/2010 | Durgin | 606/191 |
| 7,740,793 | B2 * | 6/2010 | Herweck et al. | 264/573 |
| 2001/0000348 | A1 * | 4/2001 | Chu et al. | 606/113 |
| 2001/0034518 | A1 | 10/2001 | Edwards | |
| 2002/0025327 | A1 | 2/2002 | Schmidt | |
| 2002/0082469 | A1 * | 6/2002 | Taheri | 600/37 |
| 2002/0183740 | A1 | 12/2002 | Edwards et al. | |
| 2003/0023287 | A1 * | 1/2003 | Edwards et al. | 607/101 |
| 2003/0036804 | A1 | 2/2003 | Thomas et al. | |
| 2003/0073902 | A1 | 4/2003 | Hauschild et al. | |
| 2003/0165541 | A1 | 9/2003 | Donovan | |
| 2004/0002747 | A1 * | 1/2004 | Ryan et al. | 607/101 |
| 2004/0015100 | A1 | 1/2004 | Schmidt | |
| 2004/0044308 | A1 * | 3/2004 | Naimark et al. | 604/103 |
| 2004/0064093 | A1 * | 4/2004 | Hektner et al. | 604/103.01 |
| 2004/0067235 | A1 | 4/2004 | Doshi | |
| 2004/0087893 | A1 | 5/2004 | Kwon | |
| 2004/0092875 | A1 | 5/2004 | Kochamba | |
| 2005/0033236 | A1 | 2/2005 | Wijay et al. | |
| 2005/0065483 | A1 * | 3/2005 | Nakao | 604/264 |
| 2007/0129735 | A1 * | 6/2007 | Filipi et al. | 606/144 |
| 2008/0033290 | A1 * | 2/2008 | Saadat et al. | 600/433 |

* cited by examiner

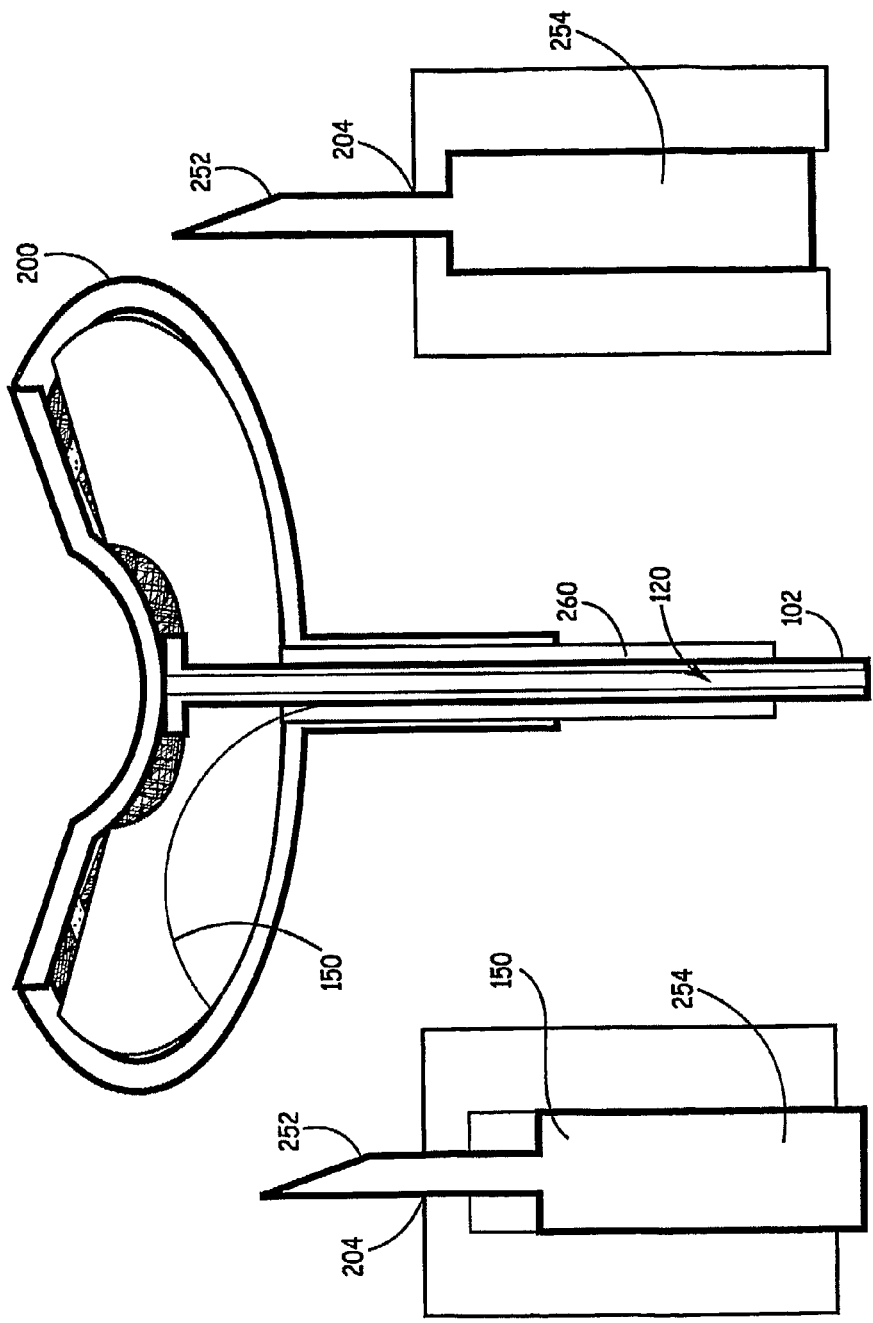

INJECTION GUIDANCE SYSTEM AND METHOD

CLAIM OF PRIORITY

This non-provisional application claims the benefit of U.S. provisional application No. 60/688,213 filed Jun. 7, 2005, and incorporated herein by reference in its entirety.

FIELD OF THE INVENTION

The invention relates to an apparatus and method of treating urinary incontinence and more particularly to a minimally invasive injection guidance system and method of treating urinary incontinence that can be utilized in various medical settings such as a clinic.

BACKGROUND

Every year millions of men, women, and children of all ages suffer from urinary incontinence or involuntary loss of urinary control. For those suffering from urinary incontinence their lives are perpetually interrupted by thoughts of ensuring they have ready access to a restroom. Everyday activities such as visiting a movie theater or attending a sporting event can become unpleasant. Sufferers often begin to avoid social situations in an effort to reduce the stress associated with their condition.

There are five basic types of incontinence: stress incontinence, urge incontinence, mixed incontinence, overflow incontinence and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "overactive bladder" comprising the symptom of urgency, frequency with or without incontinence, usually with noturia in the absence of a contributing urological condition. This symptom complex is also associated with the terms "hyperactive bladder," "frequency/urgency syndrome" or "irritable bladder," occurs when an individual experiences the compelling need to urinate and loses bladder control before reaching the toilet. Urge incontinence can take the form of neurogenic detrusor hyperflexia, detrusor sphincter dyssnerigia, overactive bladder, benign prostatic hyperplasia (enlarged prostate), bladder neck obstruction and/or interstitial cystitis. Mixed incontinence is a combination of the symptoms for both stress and urge incontinence. Mixed incontinence is the most common form of urinary incontinence. Inappropriate bladder contractions and weakened sphincter muscles usually cause this type of incontinence. Overflow incontinence is a constant dripping or leakage of urine due to an overfilled bladder. Functional incontinence results when a person has difficulty moving from one place to another. It is generally caused by factors outside the lower urinary tract, such as deficits in physical function and/or cognitive function.

The bladder is composed of several layers of tissue which includes an 1) inner mucosal and submucosal layer, 2) a muscular layer composed of smooth muscle—the "detrusor", and 3) a serosal layer. It is the muscosa and submucosa that contains many of the sensory nerves responsible for afferent sensory input that is associated with both sensation experienced as fullness or pain and is associated with the symptoms of urgency and frequency and that results in reflex efferent activity and detrusor contraction resulting in the sensory symptoms above and a rise in intravesical pressure that may result in incontinence.

A variety of treatment options are currently available to treat overactive bladder and incontinence. Some of these treatment options include external devices, behavioral therapy (such as biofeedback, electrical stimulation, or Kegel exercises), injectable materials, prosthetic devices and/or surgery. Surgery may take the form of intestinal augmentation of the bladder, implantation of a neuromodulator on the peripheral sacral nerves, or endoscopic injection of the detrusor. Depending on the age, medical condition, and personal preference, current surgical procedures can also be used to completely restore continence. However, as with any surgery there can be instances of long recovery periods and potential complications.

What is needed in the industry is a minimally invasive surgical system and method of treating overactive bladder in both male and female patients, that 1) provides a controlled pattern of injection, 2) provides a controlled number of injection sites, 3) provides a controlled depth of injection, 4) provides a controlled amount of injection, 5) makes endoscopy optional, and 6) that can be conducted on an inpatient or outpatient basis and lastly 7) exposes the patient to very little physical discomfort during the procedure.

SUMMARY OF THE INVENTION

A non-invasive medicinal or pharmaceutical delivery system particularly suitable for treating patients with the syndrome of "overactive bladder with or without incontinence is described herein that achieves the above described needs in the industry.

In one example embodiment of the invention, the system comprises a catheter having at least one injection guide operatively disposed proximate an end of the catheter and at least one needle that is extendable through the catheter and the injection guide to deliver a medicinal compound or pharmaceutical to the tissues (muscosa and/or submucosa and/or musculature) of the bladder. The medicinal compound or pharmaceutical acts on the tissue to reduce and/or prevent Over Active Bladder ("OAB") and incontinence by injection into the inner, middle, or outer layers of the bladder. The device may be utilized to deliver antibiotic, chemotherapeutic, anti-neoplastic, anti-inflammatory or other types of compounds by varying the number, the pattern, and the depth of the injections.

In another example embodiment, the injection guide comprises a balloon or inflatable structure having at least one injection needle operatively disposed in at least one channel traversing through its walls. When the injection guide is inflated the injection needle is either automatically or manually extendable from the injection guide to deliver an anesthetic, and/or medicinal and/or the pharmaceutical into the layers of the bladder.

In yet another example embodiment, the injection guide comprises an inverted generally conical structure having at least one injection needle operatively disposed in at least one channel traversing through its walls. The injection guide of this example embodiment is positionable between a pre-injection or collapsed configuration and an injection or extended configuration. The injection guide is in the pre-injection or collapsed configuration during placement into the cavity of the bladder. Once properly placed, the injection guide is extended, expanded or opened from the pre-injection configuration to the injection configuration for delivery of the needle, and correspondingly the medicinal and/or pharmaceutical, into the tissue of the bladder. When the injection guide is moved from the pre-injection configuration toward the injection configuration the injection needles may automatically or manually extend from the injection guide and penetrate the tissue of the bladder, thereby permitting a physician to deliver a pharmaceutical to the bladder tissue.

The pharmaceutical can be preloaded prior to placement of the catheter in the patient's bladder, thereby reducing the time of the procedure for the patient. The pharmaceutical can also be loaded after placement of the catheter. In either example embodiment, a pharmaceutical delivery system can be operatively coupled to the catheter to deliver or transport the pharmaceutical through the system to the patient. The needle or needles used to deliver the pharmaceutical can be flexible, resiliently flexible, semi-rigid, or rigid in their construction.

In one aspect of the invention, a bundle of needles are fed through the catheter and injection guide to inject the pharmaceutical into a number of predetermined or random bladder injection sites. A patient's discomfort can be minimized by simultaneously injecting each site.

In some example embodiments the central lumen of the rigid or flexible catheter is hollow and acts as a port for instilling or withdrawing urine, anesthetic, or additional pharmaceutical. The lumen can also be utilized for suction and may be connected to other channels in order to collapse the bladder against the injection device in order to control the pattern and depth of the injection.

In addition to controlling the sites, pattern, depth and amount of injection, the example embodiments of the invention have the advantage of reducing the time of the procedure and more particularly the amount of time the system is in the bladder cavity of the patient.

The above summary of the invention is not intended to describe each illustrated embodiment or every implementation and should therefore not be considered limiting.

BRIEF DESCRIPTION OF THE DRAWINGS

The invention may be more completely understood in consideration of the following detailed description of various embodiments of the invention in connection with accompanying figures, in which:

FIG. 5 is a partial cross section view of an injection guidance system disposed in a bladder of a patient having suction capabilities to collapse the bladder.

FIG. 6A is a first position of a needle disposed in the injection guidance system.

FIG. 6B is a second position of a needle disposed in the injection guidance system.

Figures 1A, 1B:
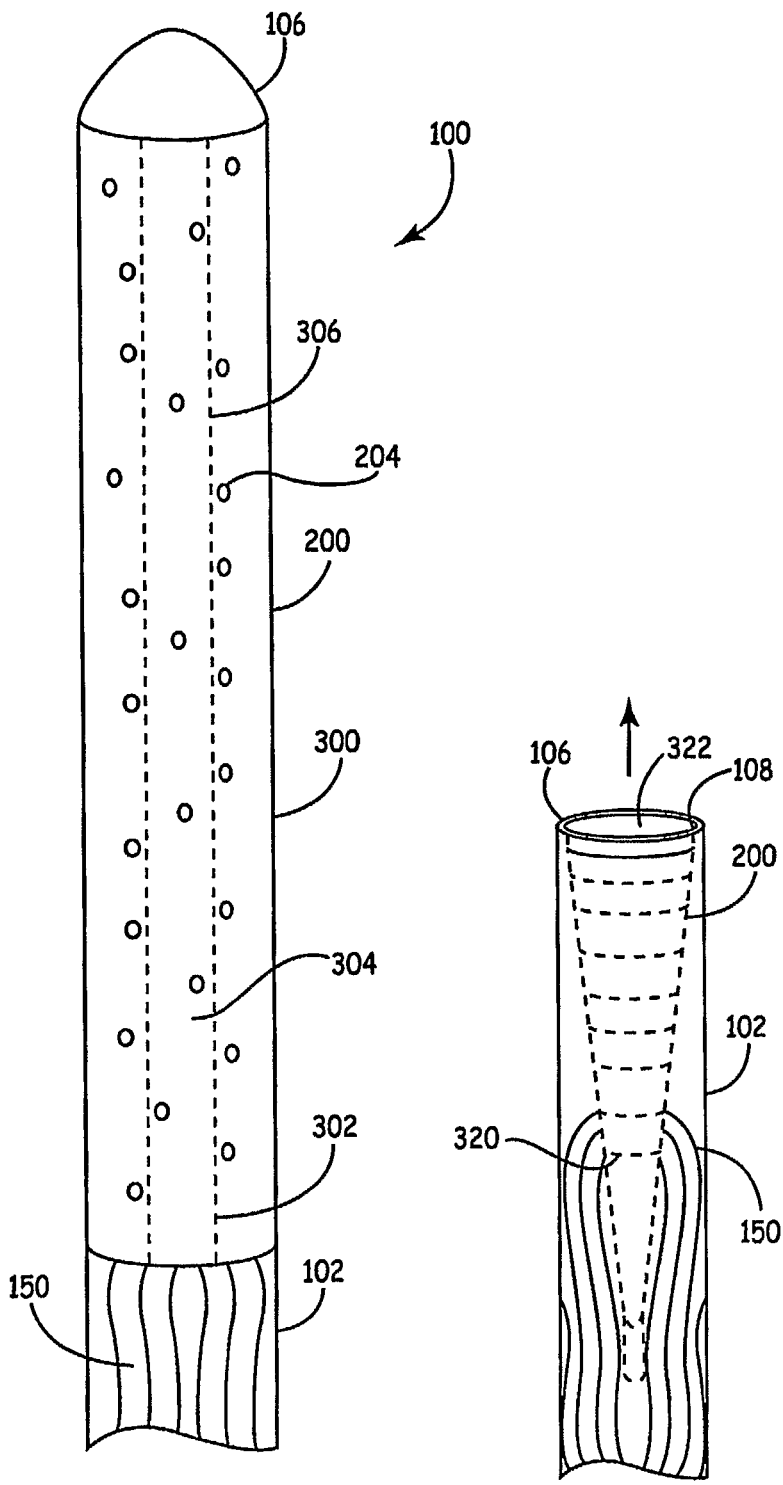
FIG. 1A is a front plan view of an injection guidance system according to an example embodiment of the invention.
FIG. 1B is a front plan view of an injection guidance system according to an example embodiment of the invention.

While the invention is amenable to various modifications and alternative forms, specifics thereof have been shown by way of example in the drawings and will be described in detail. It should be understood, however, that the invention is not to limit the invention to the particular embodiments described. On the contrary, the invention is to cover all modifications, equivalents, and alternatives falling within the spirit and scope of the invention as defined the appended claims.

DETAILED DESCRIPTION OF THE DRAWINGS

FIGS. 1, 2, 4-8C collectively illustrate an injection guidance system for delivering a pharmaceutical such as botulinum toxin to treat medical conditions such as urinary incontinence according to the invention disclosed herein. The injection guidance system is indicated as the numeral 100 in each of the example embodiments of the invention. In its essence, system 100 includes a catheter or similar device 102 operatively coupled to an injection guide 200 having at least one needle 150 disposed therein. Injection guide 200 is passed or fed through a patient's urethra until it reaches the inner cavity of the patient's bladder. Once disposed in the cavity of the bladder, injection guide 200 is transformed from a pre-injection position or configuration to an injection position or configuration. In the injection configuration injection guide 200 confronts predetermined portions of the bladder tissue, whereupon the at least one needle 150, and concurrently the pharmaceutical, is injected into the bladder tissue.

Figure 1C:
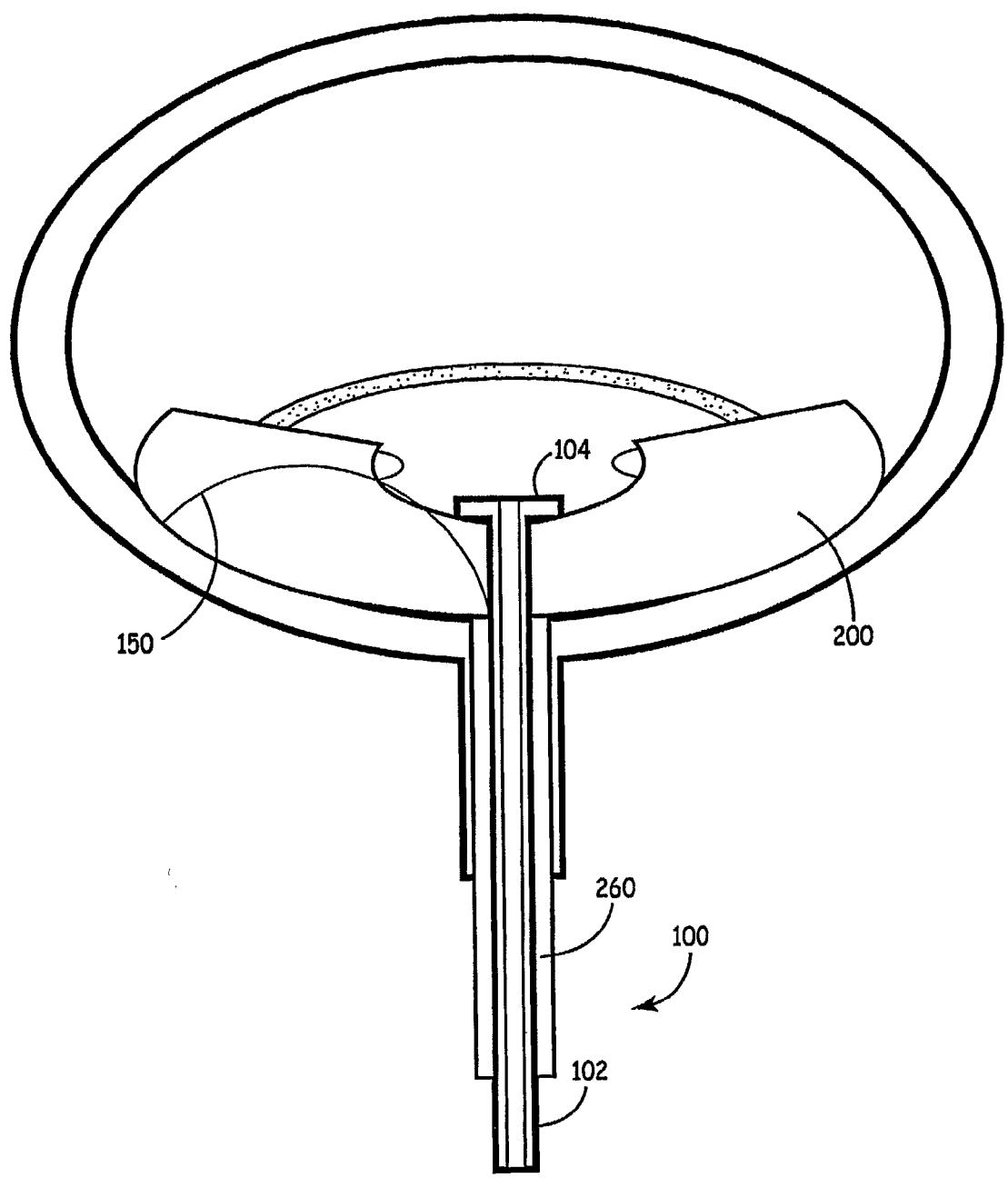
FIG. 1C is a partial cross section view of an injection guidance system according to an example embodiment of the invention.

Catheter 102 utilized in system 100 has a first end portion 104 for controlled manipulation by a physician and a second end portion 106 that is operatively coupled to or formed on injection guide 200. As illustrated in FIG. 1A-1C, second end portion 106 may be rounded, blunt, or similarly shaped and may have an aperture 108, extending into a cavity 110 thereof. First end portion 104 may include a handle (not shown) coupled to or formed thereon for manipulation by a physician. First end 104 and/or handle aid a physician in axially placing or passing catheter 102 through a patient's urethra. First end portion 104 and/or handle can also be used to move or operate injection guide 200 from the pre-injection configuration toward the injection configuration.

Figure 2A:
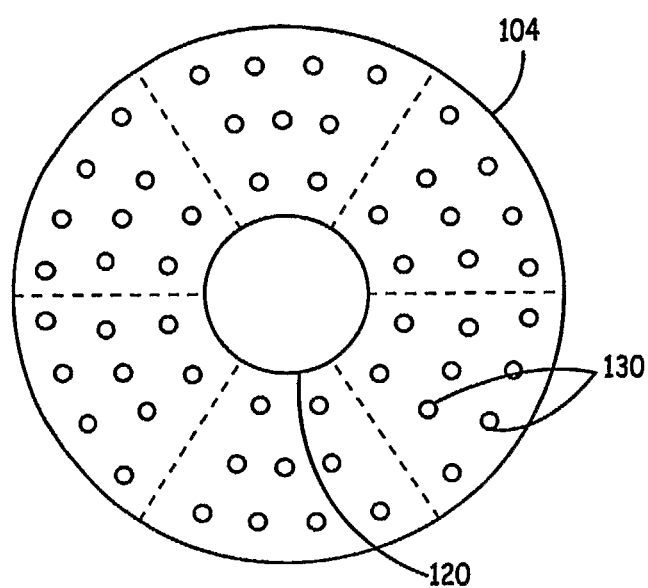
FIG. 2A is a cross section view of a catheter having a central lumen and a plurality of peripheral lumen.
Figure 2B:
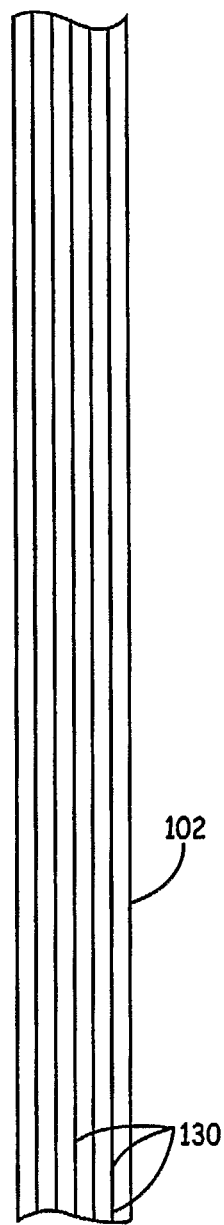
FIG. 2B is a partial plan view of a catheter in phantom.
Figure 3:
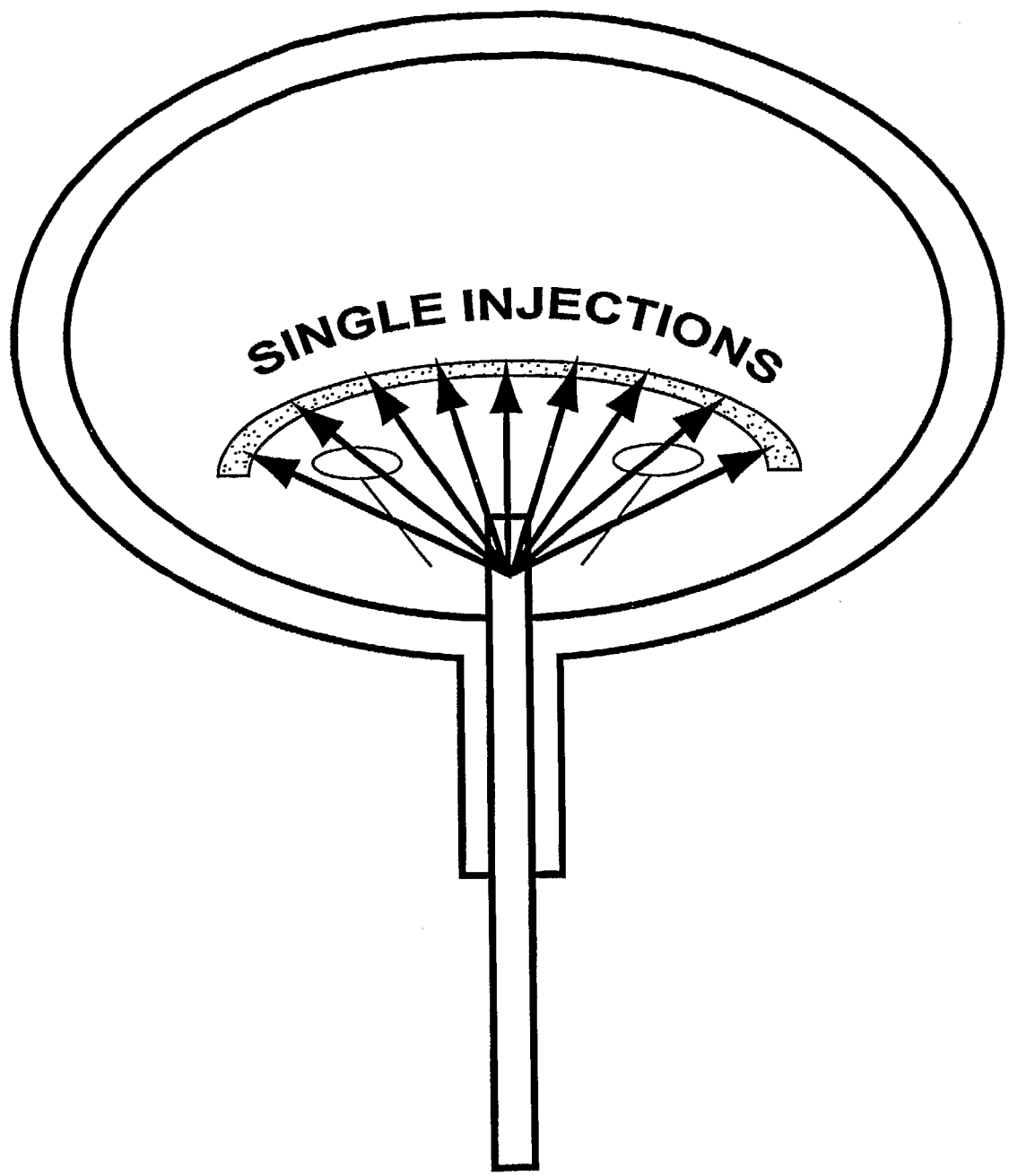
FIG. 3 is an illustration of a single injection method of the prior art.

Referring to FIGS. 2A and 2B, at least one central lumen 120 can extend axially along a length of catheter 102. Central lumen 120 can be utilized for draining the bladder of any fluids contained therein prior to or during treatment. Central lumen 120 can also be used to introduce air or other fluids in either a gas or liquid state into the cavity of the bladder. For example, saline or other cleansing fluids can be introduced into the bladder to clean the interior thereof prior to treatment. Central lumen 120 can also be utilized to draw air out of the cavity of the bladder, such as if there is a need to collapse or draw the walls of the bladder toward catheter 102 and/or injection guide 200. An endoscope camera, or other visual monitoring device can be introduced into the bladder cavity via central lumen 120 to aid a physician in observing the interior of the bladder prior to, during or after the procedure.

At least one needle 150 (as illustrated in FIGS. 1B and 1C) is operatively disposed in at least one peripheral lumen 130 that extends along a length of catheter 102 and is generally parallel to central lumen 120. In one example embodiment of the invention, multiple needles 150 are operatively disposed in corresponding peripheral lumens 130. Peripheral lumen 130 can be arranged in any pattern and any number to facilitate disposing the needles 150 in a predetermined location within the bladder.

Catheter 102 is constructed of a material that permits it to be malleable or bendable without compromising the integrity of the central 120 and/or peripheral lumens 130. For example, catheter 102 may comprise of PTFE (polytetrafluoroethylene), a braided or woven metal such as aluminum, titanium and the like. One skilled in the art will recognize that other materials either singularly or in combination may also be utilized and they should therefore be considered to be within the spirit and scope of the invention.

Referring back to FIGS. 1A-1C, injection guide 200 generally is operatively coupled or disposed proximate to second end portion 106 of catheter 102. Injection guide 200 can include varying configurations depending upon the particular needs of a physician at the time of treatment. As illustrated in FIGS. 6A and 6B, regardless of the configuration, injection guide 200 includes a plurality of channels 202 (shown in the singular) that are in registration with respective peripheral lumens 130 such that during a procedure needles 150 may traverse through peripheral lumens 130 and channels 202. Each of channels 202 terminates in an aperture or opening 204 that permits at least partial passage of needles 150 from channels 202 to engage and penetrate the tissue of the bladder.

A particular novel feature of the invention is that while catheter 102 and injection guide 200 are traversing a patient's urethra, needles 150 are kept in injection guide 200 to prevent premature injection or injury to the tissue of the urethra. Once injection guide 200 is disposed in the cavity of the bladder a physician can then move injection guide from its pre-injection configuration toward its injection configuration. Once in the injection configuration needles 150 can extend from injection guide 200 to pierce the bladder tissue. The physician can then facilitate the injection of the pharmaceutical into the tissue of the bladder. In one embodiment, a trocar of the type discussed within U.S. Pat. No. 5,152,754, which is hereby incorporated in its entirety by its reference, can be used with catheter 102, needles 150, and/or injection guide 200 to facilitate feeding needles 150 through peripheral lumens 130 and into the bladder tissue.

In an example embodiment of the invention, the depth that needles 150 are permitted to puncture the bladder tissue is controlled by the interface of injection guide 200 and needles 150. Referring to FIGS. 5-6B for example, opening 204 can have an inner diameter less than an inner diameter of channels 202 and needles 150 can have a tip portion 252 having a outer diameter slightly less than the inner diameter of opening 204 and a shaft portion 254 having an outer diameter slightly less than the inner diameter of channel 202 such that tip portion 252 extends through opening 204 and shaft portion 254 abuts or confronts injection guide 200 proximate opening 204. This configuration permits the depth of injection to be controlled by the length of tip portion 252.

System 100 can be provided to a physician or hospital as a kit including catheter 102, injection guide 200, needles 150 and the pharmaceutical. As a kit, needles 150 can come pre-loaded in injection guide 200 and catheter 102 or they can come as distinct components. When provided as a distinct component, a physician can select the injection configuration by inserting needles 250 into any of the particular peripheral lumen 130. By selecting particular peripheral lumen 130 a physician can predetermine where needles 250 will exit injection guide 200 and puncture a predetermined location of bladder tissue. The ability to select a particular peripheral lumen 130 configuration and the orientation of injection guide 200 in the bladder permits a physician to conduct the procedure without the need of an endoscope or like visual monitoring devices.

Figure 7A:
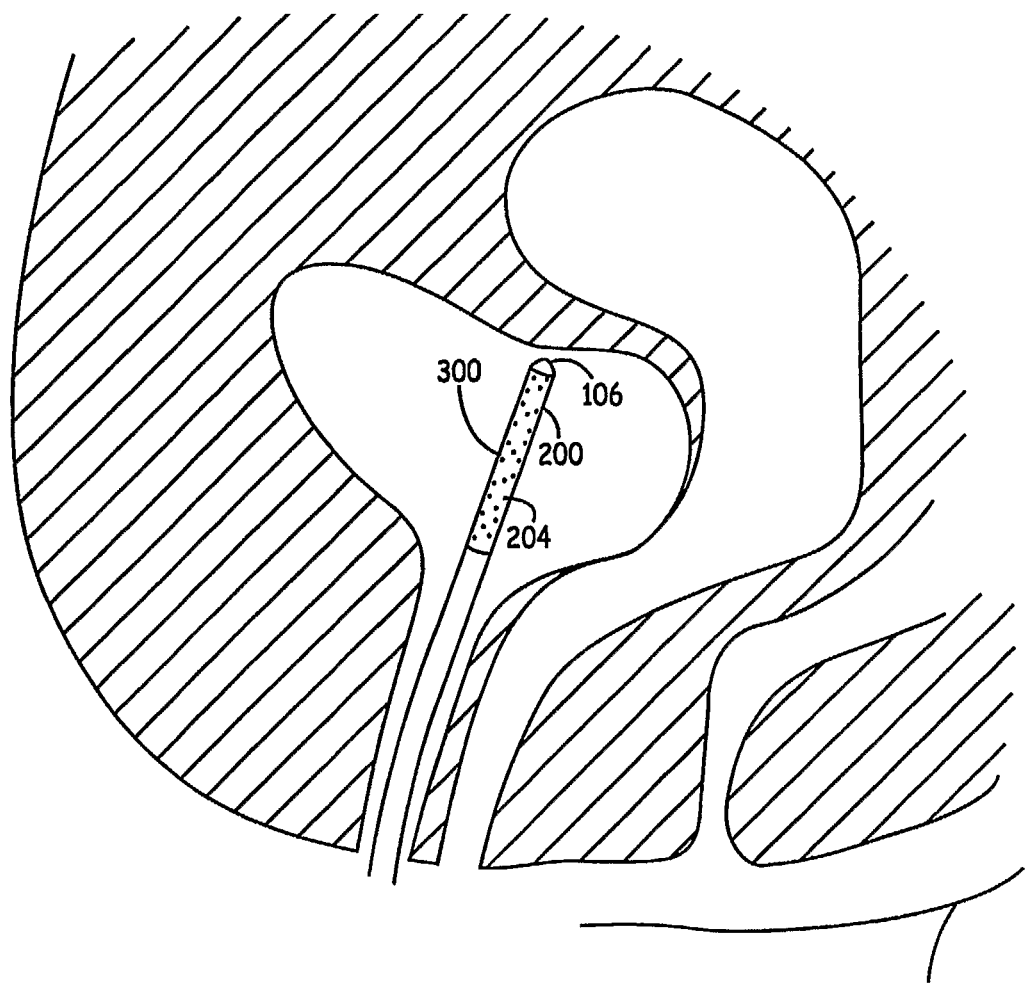
FIG. 7A is a cross section view of a human bladder having an example embodiment of the injection guidance system disposed therein in a pre-injection configuration.
Figure 7B:
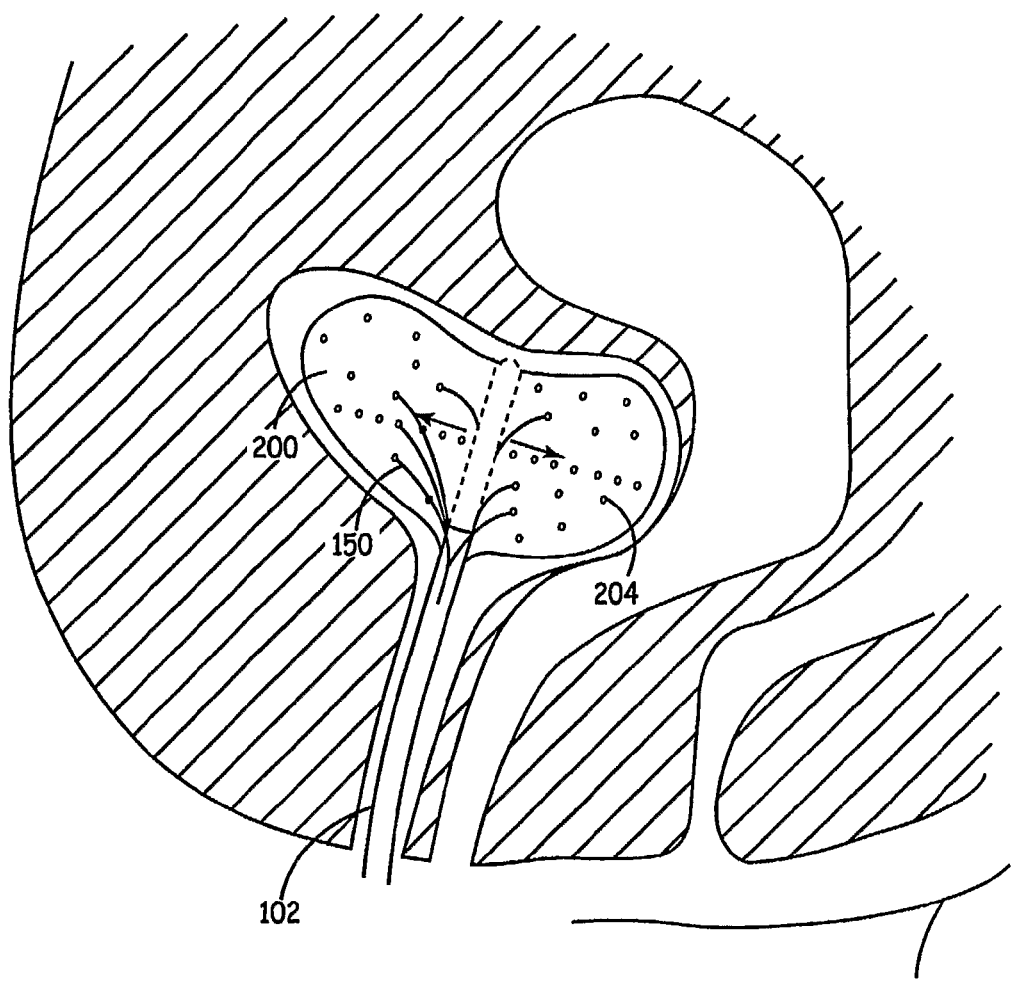
FIG. 7B is a cross section view of a human bladder having an example embodiment of the injection guidance system disposed therein in an injection configuration.

Multiple injection guide 200 configurations are envisioned to be used with system 100 depending upon the particular needs of the physician and patient. In one example embodiment, as illustrated in FIGS. 1A, and 7A-7B, injection guide 200 can comprise an inflatable (or expandable sheet structure) membrane 300 disposed about a shaft 302 having a axial passageway 304 extending therethrough. Shaft 302 includes multiple spaced apertures 306 extending therethrough that are in fluid communication with axial passageway 304. Axial passageway 304 is in fluid communication with central lumen 120 such that air flowing through central lumen 120 and axial passageway 304 flows through apertures 306 and inflates the inflatable membrane 300.

As illustrated in FIG. 7A, during placement of injection guide 200 in the patient's bladder inflatable membrane 300 is in the pre-injection or deflated configuration. Once positioned in the patient's bladder the physician can release a fluid such as air, $CO_2$, and the like through central lumen 120 to inflate the inflatable membrane 300. As illustrated in FIG. 7B, inflatable membrane 300 can expand to fill at least a portion of the patient's bladder cavity. An outer surface of inflatable membrane 300 engages or confronts the inner surface of the bladder wall at predetermined locations. As described above, needles 150 are either already operatively disposed in peripheral lumen 130 and/or channels 202 or they can be inserted by the physician. If already present, needles 150 can either be manually inserted into the bladder tissue through openings 204 of inflatable membrane 300 or they can be automatically extended during transformation from the pre-injection configuration toward the injection configuration. If needles 150 are manually inserted into the bladder tissue a trocar, as described above, may be used. In another embodiment, catheter 102 extends longitudinally through inflatable membrane 300. Second end 106 of catheter 102 can be open such that fluids can be removed from or inserted into the cavity of the bladder.

The inflatable membrane 300 can comprise any resiliently flexible material such as rubber and the like. Those skilled in the art will appreciate that numerous materials individually or in combination can be used to manufacture inflatable membrane 300. The various materials should therefore be considered to be within the spirit and scope of the invention.

Depending upon the configuration, injection guide 200 confronts at least a predetermined portion or section of the tissue of the bladder. As injection guide 200 confronts the predetermined section of bladder tissue openings and apertures 204 are positioned and patterned generally adjacent to the predetermined section of the bladder tissue such that needles 150 and concurrently or subsequently the pharmaceutical may be precisely injected into the tissue of the bladder.

Figure 8A:
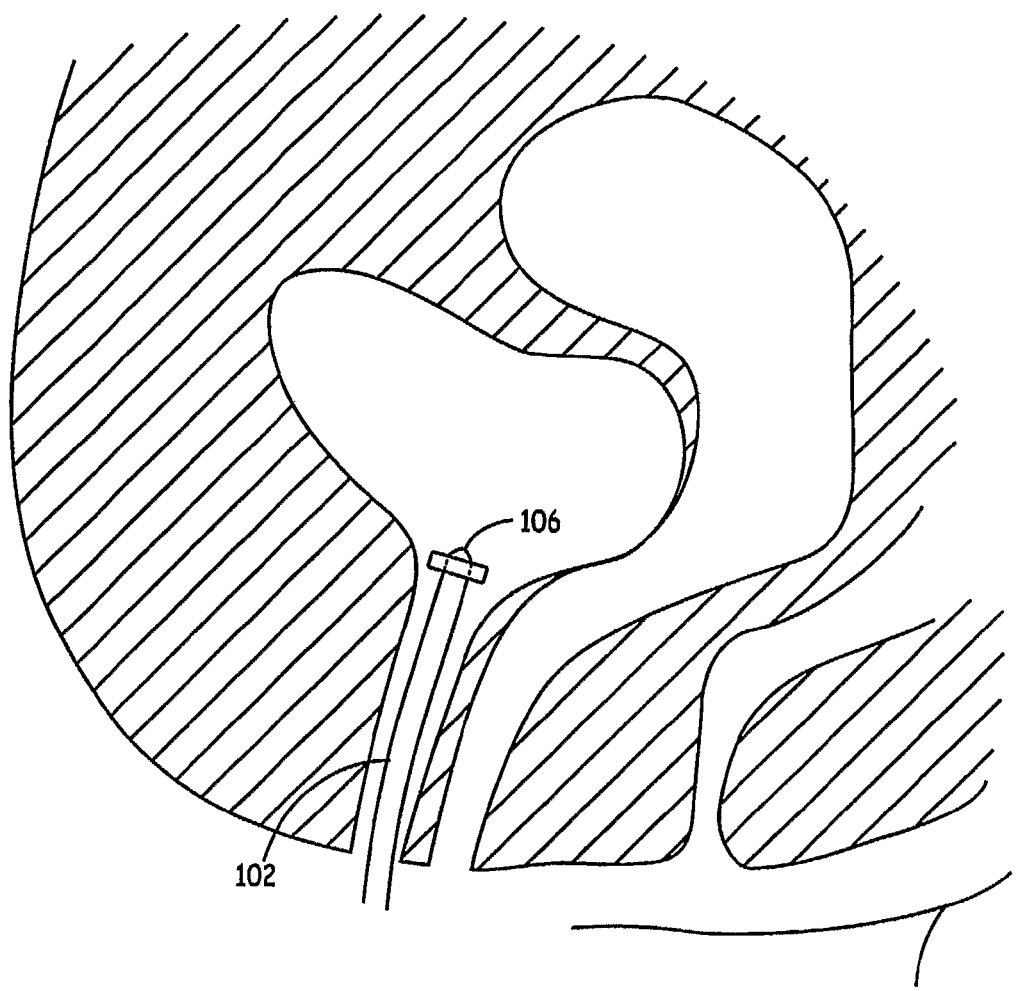
FIG. 8A is a cross section view of a human bladder having an example embodiment of the injection guidance system disposed therein in a pre-injection configuration.
Figure 8B:
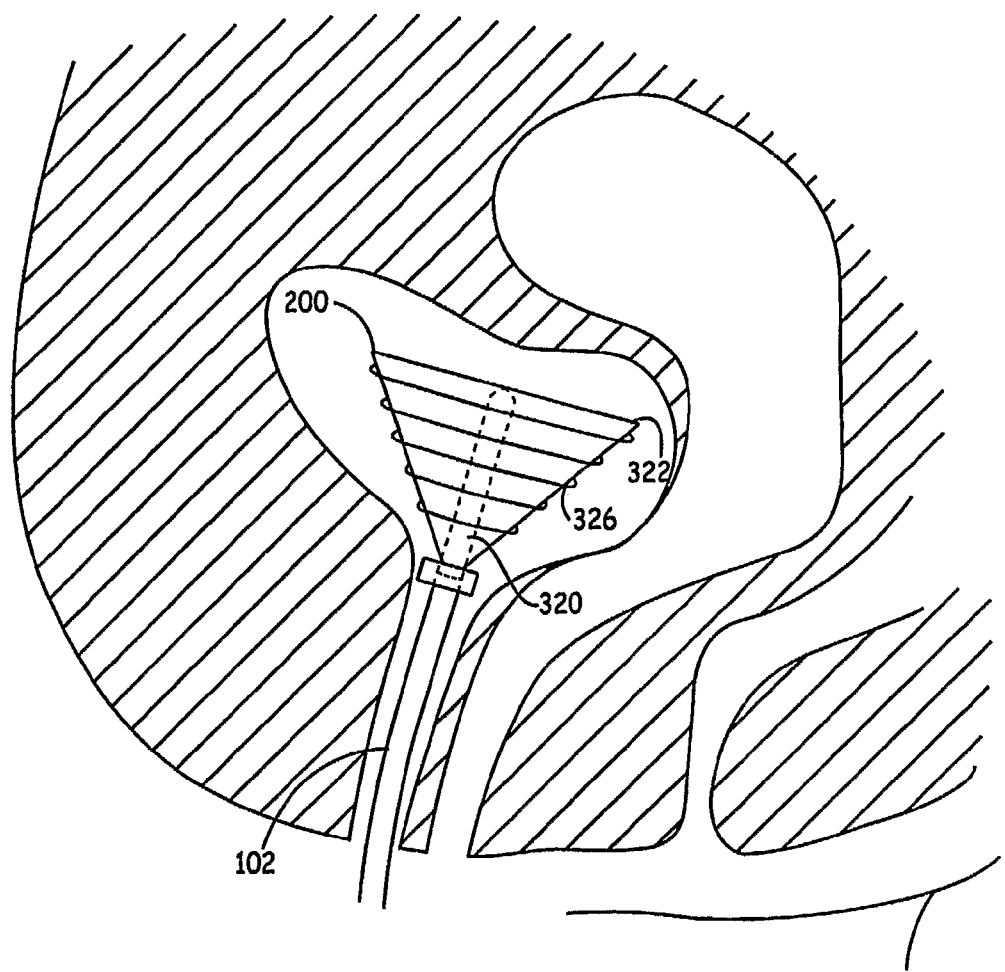
FIG. 8B is a cross section view of a human bladder having an example embodiment of the injection guidance system disposed therein in an injection configuration.

In another example embodiment of the invention, as illustrated in FIGS. 1B, and 8A-8C, injection guide 200 can comprise a generally retractable conical structure having a generally narrower first end 320 operatively coupled to catheter 102 and an opposed generally wider second end 322. As particularly illustrated in FIGS. 1B and 8A, during placement of catheter 102 through the patient's urethra and bladder cavity injection guide 200 is retracted or sheathed in the central lumen 120 of catheter 102 in the pre-injection configuration. Once catheter 102 is disposed in the bladder cavity, a physician can move injection guide 200 from the pre-injection configuration toward the injection configuration as illustrated in FIG. 8B. A trocar device described above may be utilized to move injection guide 200 and/or needles 150 from the pre-injection configuration toward the injection configuration.

Figure 8C:
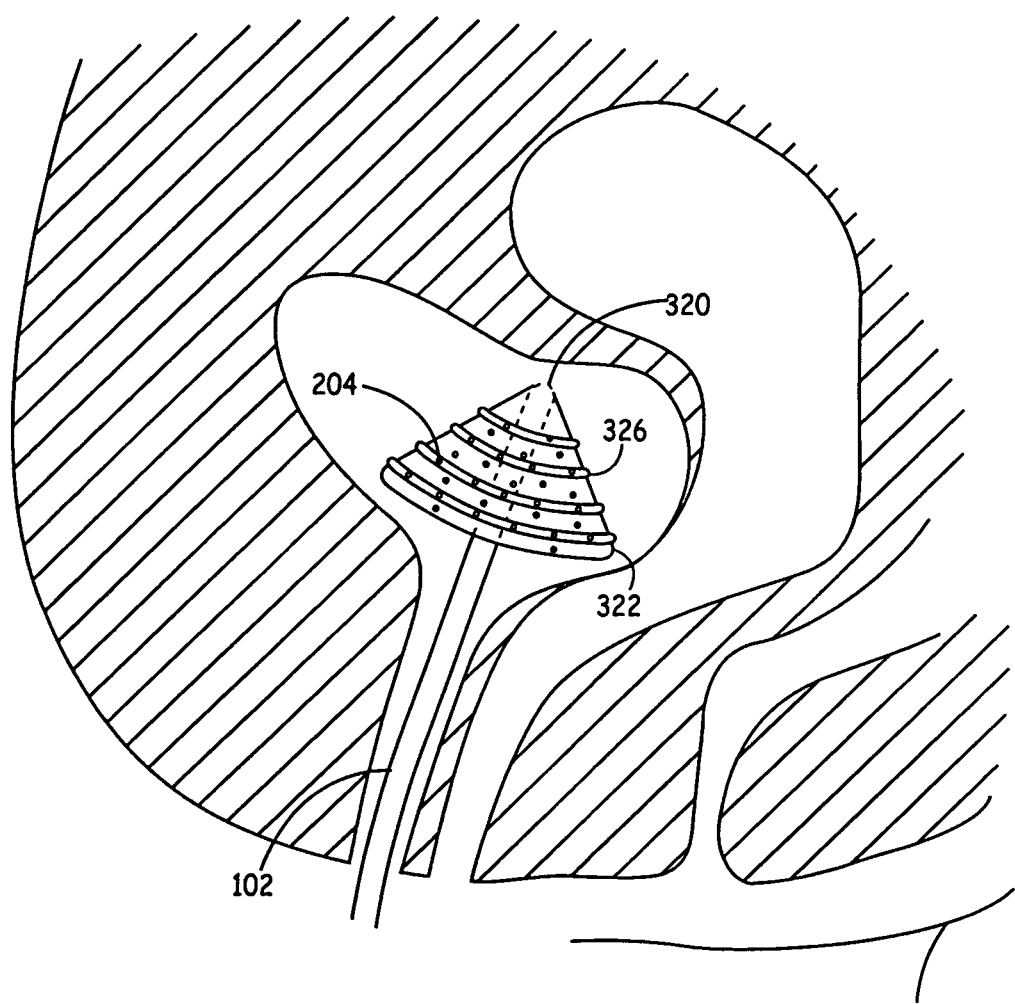
FIG. 8C is a cross section view of a human bladder having an example embodiment of the injection guidance system disposed therein in an injection configuration.

As illustrated in FIGS. 8B and 8C, injection guide 200 can include multiple spaced rings or annular portions 326 formed or disposed thereon for guiding needles 150 to the bladder tissue. Annular portions 326 can also provide generally automatic expansion or extension of injection guide 200 as it moves from the pre-injection configuration toward the injection configuration. As particularly illustrated in FIG. 8C, openings or apertures 204 can be spaced about a periphery of annular portions 326 such that needles in channels 202 are extendable therethrough to a predetermined bladder tissue location. Needles 150 may also extend from any portion of injection guide 200 and is not limited to annular portions 326. In place of annular portions 326, linear portions (not shown) can extend between first end 320 and second end 322 of injection guide 200. Other configurations are also contemplated by the invention and should also be considered to be within the spirit and scope of the invention.

An example of another contemplated embodiment is illustrated in FIG. 8C, where second end 322 of injection guide 200 extends over at least a portion of catheter 102 similar to an umbrella. In this contemplated embodiment, the pre-injection configuration of injection guide 200 is defined by injection guide 200 being disposed closely about catheter 102 for placement into the patient's urethra and bladder. Once properly position, a physician can operatively move injection guide 200 from the pre-injection configuration toward the injection configuration as illustrated in FIG. 8C. In the injection configuration, needles 150 can be extended through injection guide 200 and into the tissue of the bladder.

In either of the above described configurations, injection guide 200 can comprise a generally flexible material such as rubber, latex and the like. Annular portions 326 can comprise a generally more rigid material or a generally flexible material and a resiliently flexible insert such as a metal or plastic wire. Various mechanical configurations can be utilized to move injection guide 200 between the pre-injection and injection configurations. One skilled in the art will recognize that levers, hinges, and the like can be utilized to move injection guide 200 between the pre-injection and injection configurations.

In either of the immediately preceding embodiments, at least a portion of apertures 204 can be utilized for suction to draw the walls of the bladder toward the catheter 102 and/or injection guide 200. In this example embodiment, any of the peripheral lumens 130 not occupied by a needle 150 can be used for suction. In another example embodiment of the invention, second end portion 106 of catheter 102 can be open to act as a suction to draw the walls of the bladder toward injection catheter 102 and/or injection guide 200.

Once the pharmaceutical has been injected into the bladder tissue, needles 150 can be withdrawn into injection guide 200. Injection guide 200 can then be moved from the injection configuration to the pre-injection configuration for withdraw from the bladder and urethra.

Figure 4:
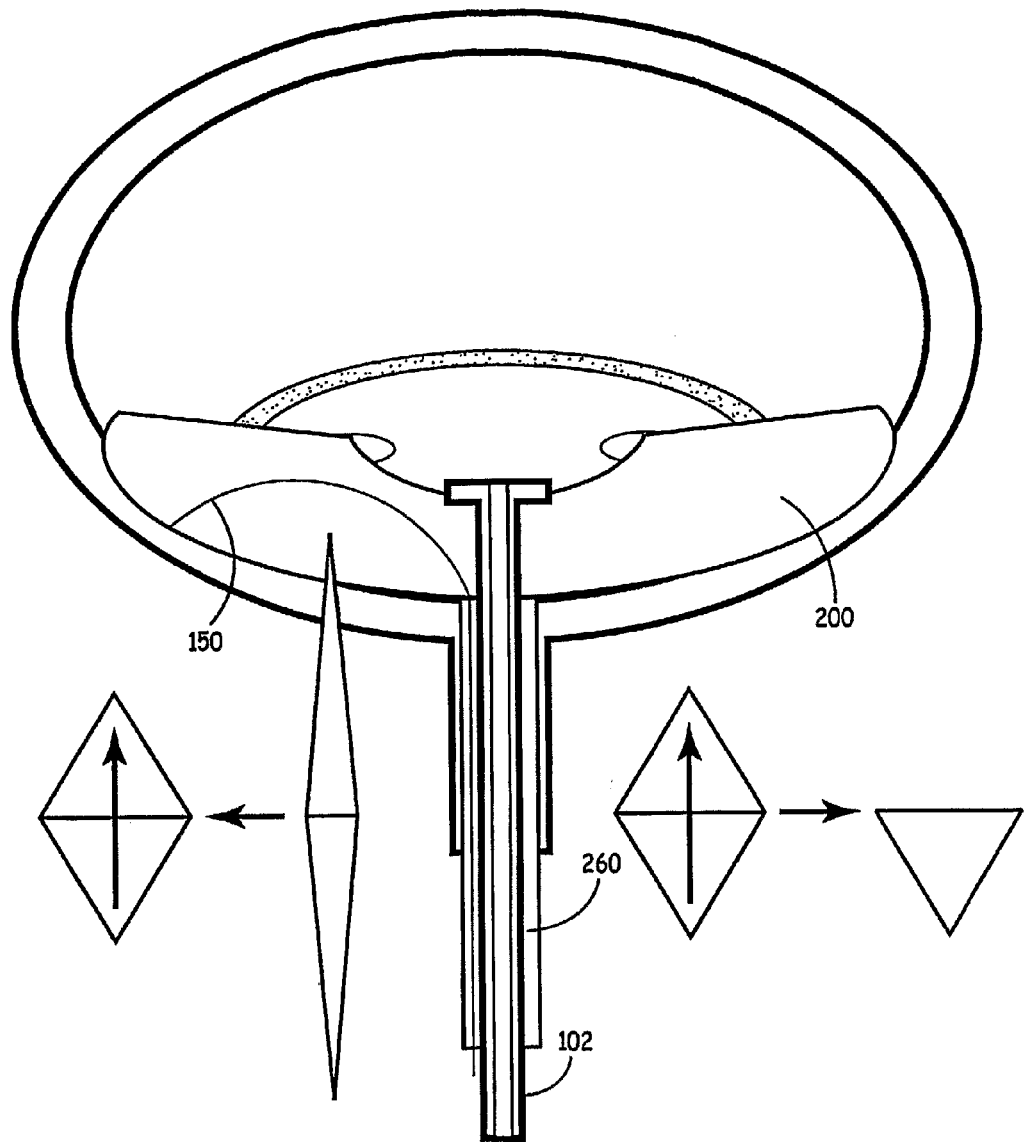
FIG. 4 is a partial cross section view of an injection guidance system disposed in a bladder of a patient having a needle fed therethrough.

In another example embodiment, as illustrated in FIGS. 1C, 4, and 5, injection guide 200 has a generally saddle configuration that is foldable between the pre-injection configuration (not shown) and the injection configuration. In this example embodiment, injection guide 200 can be disposed about or in catheter 102. Referring to FIG. 4, injection guide 200 can be moved between the pre-injection and injection configurations by pushing or pulling on a stem portion 260 of injection guide 200 extending beyond the patient. Prior to inserting injection guide 200 through the patient's urethra and bladder, the physician pulls on stem portion 260 to collapse or fold injection guide 200 into the pre-injection configuration. As illustrated in FIG. 5, once injection guide 200 is positioned in the bladder suction can be applied through central lumen 120 of catheter 102 to draw the bladder toward and about the injection guide 200. Needles 150 can be pushed or extended through openings 204 and into the bladder tissue. The pharmaceutical is then injected into the bladder tissue. The physician then pulls on stem portion 260 to fold injection guide 200 into the pre-injection configuration whereby catheter 102 and injection guide 200 can be safely and comfortably removed from the patient.

Details of the invention may be modified in numerous ways without departing from the spirit and scope of the invention. For example, numerous materials can be utilized in the manufacture of catheter 102 and injection guide 200. Additionally, numerous configurations of injection guide 200 are contemplated with a few example embodiments being described above for illustration. Numerous operative assemblies can also be utilized for moving injection guide 200 between the pre-injection and injection configurations. Needles 150 can be manufactured from numerous materials resulting in flexible, semi-flexible, semi-rigid, and rigid needles of varying gauges. Although the invention has been described with reference to particular embodiments one skilled in the art will recognize that changes may be made in form and detail without departing from the spirit and scope of the invention. Therefore, the illustrated example embodiments should be considered in all respects as illustrative and not restrictive.

What is claimed is:

1. An injection guidance system for delivering a pharmaceutical in the treatment of a human or animal organ, the system comprising:
   (a) a catheter having at least one peripheral lumen extending longitudinally therein;
   (b) at least one injection needle operatively extended through the at least one peripheral lumen between a retracted position and an extended position;
   (c) an inflatable member having an inflatable membrane with an interior surface and an exterior surface, the inflatable member being disposed from the exterior of the catheter that is selectively expanded by means of a gas or liquid fluid from a collapsed configuration to a three-dimensionally expanded configuration extended from the catheter, such inflatable member having at least one aperture within its surface wall extending from the exterior surface of the membrane to its interior surface, so as to communicate with the interior of the inflatable member for passage of the injection needle therethrough;
   (d) wherein the catheter is inserted into the organ with the inflatable member in its collapsed configuration with the injection needle in its retracted position; and
   (e) wherein, once inside the organ, the inflatable membrane is expanded by means of the gas or liquid fluid to its three-dimensional expanded configuration to bring its surface wall proximate to the organ tissue wall, and automatically extend the injection needle during the expansion of the inflatable member from its collapsed configuration to its expanded configuration to penetrate the organ tissue wall at a predetermined location, the aperture or the injection needle positioned inside the aperture coming into contact with the gas or liquid fluid.

2. The injection guidance system of claim 1, wherein the inflatable member comprises an inverted or upright conical shape.

3. The injection guidance system of claim 1 further comprising a central lumen extending longitudinally along at least a portion of the catheter.

4. The injection guidance system of claim 1, wherein the inflatable member includes a plurality of apertures and a plurality of injection needles extending therethrough to generally simultaneously treat a region of the organ tissue wall.

5. The injection guidance system of claim 4, wherein the plurality of injection needles form a pattern to deliver the pharmaceutical to a generally predetermined location on the organ tissue wall.

6. The injection guidance system of claim 1, wherein the catheter is constructed of a malleable material that permits it to bend without compromising the integrity of the peripheral lumen.

7. The injection guidance system of claim 3, wherein the inflatable member is stored inside the central lumen inside the catheter when in its collapsed configuration.

8. The injection guidance system of claim 3 further comprising a suction device in operative communication with the central lumen, wherein fluid existing within the organ may be withdrawn into the catheter.

9. The injection guidance system of claim 1 further comprising a suction device in operative communication with at least one peripheral lumen, wherein the organ tissue wall may be drawn towards the inflatable member or injection needle.

10. The injection guidance system of claim 1, further comprising a trocar operatively coupled to the catheter and the at least one injection needle to facilitate feeding the at least one injection needle into the interior of the organ.

11. The injection guidance system of claim 1, wherein the aperture within the surface wall of the expandable member has a diameter generally less than a portion of the injection needle, thereby controlling the extension of the injection needle beyond the outside surface of the inflatable member.

12. The injection guidance system of claim 1, wherein air or a fluid passing through a lumen within the catheter extends the inflatable member to its expanded configuration.

13. A needle injection guidance kit used to treat the tissue of organs such as the bladder, the kit comprising an injection guidance system of claim 1, and at least one pharmaceutical that is deliverable by the at least one injection needle to the tissue being treated.

14. The kit of claim 13, wherein the pharmaceutical is pre-loaded in the injection needle.

15. The kit of claim 13, wherein the inflatable member has a pre-defined configuration to facilitate injection of the pharmaceutical into generally predetermined locations of the organ tissue.

16. The kit of claim 13, further comprising a trocar for feeding the at least one injection needle into the interior of the organ.

17. The injection guidance system of claim 1, wherein the inflatable member comprises a saddle shape.

18. The injection guidance system of claim 2 further comprising at least one spaced ring or annular channel disposed along or formed within the surface wall of the inflatable member for directionally guiding the injection needle extending through the associated aperture within the surface wall.

19. The injection guidance system of claim 1, wherein the organ is a bladder.

20. The injection guidance system of claim 1 further comprising a suction device in operative communication with the central lumen, wherein the organ tissue wall may be drawn towards the inflatable member or injection needle.

* * * * *